United States Patent [19]  [11] 4,355,056
Dalla Betta et al.  [45] Oct. 19, 1982

[54] METHOD OF MANUFACTURING A COMBUSTIBLES SENSOR

[75] Inventors: Ralph A. Dalla Betta, Mountain View, Calif.; Sharon L. Zimmerlin, Chagrin Falls, Ohio

[73] Assignee: The Babcock & Wilcox Company, New Orleans, La.

[21] Appl. No.: 249,308

[22] Filed: Mar. 31, 1981

[51] Int. Cl.³ .................. G01N 31/12; B05D 5/12; H01L 7/00
[52] U.S. Cl. .................. 427/126.4; 23/232 E; 338/34; 422/94
[58] Field of Search .................. 427/126.4; 338/34; 422/94; 23/232 E

[56] References Cited

U.S. PATENT DOCUMENTS 3,867,207 2/1975 Decker .................. 148/6.14 R
4,242,303 12/1980 Takahashi et al. .................. 338/34 X
4,297,192 10/1981 Shinohara et al. .................. 427/126.4 X

OTHER PUBLICATIONS

Valvo Berichte, XVIII, Heft (1974), pp. 84–87.
Ullmann's Encylopedia of Technical Chemistry, 3rd Edition, vol. 18, (Munich–Berlin–Vienna 1967), p. 640.

Primary Examiner—Michael R. Lusignan
Attorney, Agent, or Firm—Vytas R. Matas; Robert J. Edwards

[57] ABSTRACT

A method of manufacturing a differential thermocouple combustibles sensor is disclosed which makes the sensor relatively insensitive to sulfur poisoning. To accomplish this the catalytic thermocouple junction of a catalytic-non-catalytic junction pair is formed by coating it with a gel to increase the surface area and then with a chloroplatinic acid solution to make it catalytic. The catalytic junction is then treated with $H_2S$ to achieve a high catalyst surface area.

10 Claims, No Drawings

METHOD OF MANUFACTURING A COMBUSTIBLES SENSOR

TECHNICAL FIELD

The present invention relates to the manufacture of gas sensors generally and in particular to the manufacture of accurate combustible gas sensors.

BACKGROUND ART

Combustible gas sensors for the measurement of high levels of gases such as CO and $H_2$ have been prepared in the past. These sensors operate by measuring a temperature differential developed when the combustible gas is catalytically reacted with oxygen at the sensor. Previous devices of this type are prone to a number of disadvantages: Rapid deactivation of the catalyst at high temperature results in an output signal of decreasing magnitude. Deterioration of the catalytic coating causes a loss in output accuracy with the passage of time. Low levels of $SO_2$ poison the catalytic coating and lead to interference if this gas is present.

These disadvantages of the prior art devices combine to limit the usefulness and applicability of catalytic combustible gas sensors. For example, in the monitoring of boiler flue gas to permit control of the effluent to a required level, the combustible gas sensor must operate in a stable manner over long periods of time, and must be insensitive to a variety of interfering gases such as $SO_2$ and NO and other contaminants that might arise from the combustion of the used fuel. In practice, it is found that combustible gas sensors prepared using prior art methods will measure combustible gases, typically CO and $H_2$, and give reasonable operating life if operated in the temperature range of 150°–260° C. (300° to 500° F.). However, in the presence of even low levels of $SO_2$ (500 ppm), these sensors show a greatly reduced output due to poisoning of the catalytic surface. Some insensitivity to $SO_2$ poisoning can be gained by using a higher operating temperture, but this results in short sensor life. Also, a high operating temperature can lead to a decreased measuring span due to activity of the reference junction and erratic sensor output in the presence of $SO_2$ and NO.

SUMMARY OF THE INVENTION

The combustibles gas sensors made by the method of this invention overcomes all of the disadvantages of the prior art devices as well as others by producing a very high surface area platinum catalyst as the catalytic coating on the sensor which is able to operate at elevated temperatures and is insensitive to $SO_2$ poisoning. This coating was found to be stable in very high temperatures giving the manufactured detector a high temperature operating capability without the degradation of performance found in prior art devices. Further, when combined with a unique totally inactive coating for the reference portion of the sensor, this sensor can be operated at the mentioned high temperatures for long periods of time remaining insensitive to contaminants such as $SO_2$ and NO.

The manufactured device of this invention consists of at least two opposing temperature measuring devices operated such that the output is not a function of the individual sensor temperature but is instead a function of the temperature differential between the catalytic and reference portions of the sensor. Thermocouples, resistance thermometers, thermistors, or other temperature sensitive devices can be used as the individual sensors. No matter what type of devices are used, alternating temperature measuring devices are coated according to the present method; one with a high surface area oxidation catalyst and the other with an inactive coating. The active catalyst coating acts to catalyze the exothermic oxidation of combustible gases such as CO and $H_2$ while the inactive device remains insensitive thereto. The heat liberated in the alternating devices results in a temperature differential between catalytic and reference temperature measuring devices.

The particular method of applying the catalytic coating on the active sensor according to the invention consists of first applying a high surface area $\gamma$-alumina substrate to the thermocouple or other temperature measuring device. The $\gamma$-alumina coating is applied at a thickness of 0.01 to 0.5 mm using an aqueous $\gamma$-alumina slurry. Upon drying and calcining in air, the $\gamma$-alumina forms a strong adherent coating of high surface area $\gamma$-alumina. The coating should have a surface area of 10 to 700 $m^2g^{-1}$, preferably from 50 to 700 $m^2g^{-1}$ and most preferable 100 to 500 $m^2g^{-1}$. Other refractory oxides can be used including silica, titania, magnesia, thoria, zirconia, chromia; mixed oxides such as silica-alumina, silica-zirconia, alumina-titania, alumina-chromia, etc., and even ternary oxides; crystalline aluminosilicate zeolite materials such as erionite, mordenite, faujasite and natural clays such as montmorilonite. These materials must have contaminant levels, such as Na, reduced by extraction or exchange by treatment with $NH_4OH$ to minimize deactivation of the oxidation catalyst by poisoning.

A platinum or other oxidation catalyst is next applied to the high surface area coating to produce a high surface area platinum coating. Preferred oxidation catalysts include the Group VIII metals, especially Pt, Pd, Ir and Rh, and combinations of the Group VIII metals. Pt and Pd and Pt/Pd combinations are preferred. The active oxidation catalyst is applied to achieve a high surface area on the oxide coating. In general, this is accomplished by applying the oxide coating to the sensor, then adding the catalyst such as platinum to the coating by impregnation. However, the oxidation catalyst can be added to the oxide powder and the oxidation catalyst supported on an oxide can then be coated onto the sensor.

On $\gamma$-alumina, the preferred method of the invention is impregnation using chloroplatinic acid in aqueous solution. Other platinum salts or other solvents such as alcohols, acetone, or combinations of these can be used as well. After the coating is impregnated with the catalyst, the sensor is dried at temperatures from 25° to 200° C., preferable from 50° to 150° C. The sensor is then calcined in air at temperatures from 250° to 700° C., preferable from 400° to 600° C. Other atmospheres such as vacuum, nitrogen, inert gases or hydrogen can be used, but air is preferred. Alternatively, the impregnated coating can be treated with gaseous $H_2S$, then dried and calcined. The preferred method of preparation involves impregnation of the high surface area $\gamma$-alumina coating with a chloroplatinic acid solution of 0.05 to 0.5 g Pt per g of total solution, preferably 0.1 to 0.3 g Pt per g of total solution.

As was mentioned, the reference junctions of the sensor must be made inactive. This is especially important when the sensor is operated at high temperature since the surface of the metal thermocouple or the outside case of a resistance thermometer can be an active catalyst for the combustion of CO. To deactivate the reference junction, a coating of low surface area α-alumina or other refractory material in the list disclosed above is applied. This coating is baked on to produce a strong adherent layer over the reference junction. Other techniques for producing an inactive reference junction include: electroplating the sensor with aluminum, silicon, titanium or other metal that forms an inactive adherent oxide coating upon oxidation; deposition of metals or oxides by sputtering or evaporation to produce a low surface area inactive oxide coating; and dipping the sensor in a melt of a metal, oxide or salt of a compound that upon decomposition yields a low surface area oxide coating that is inactive for oxidation.

In view of the foregoing it will be seen that one aspect of the present invention is to provide a method of manufacturing a high surface area combustibles sensor operable at elevated temperatures for extended periods of time.

Another aspect of the present invention is to provide a method of manufacturing a combustibles sensor which is insensitive to sulfur poisoning.

These and other aspects of the present invention will be more clearly seen from a review of the following description of the preferred embodiment.

DESCRIPTION OF THE PREFERRED EMBODIMENT

The combustibles sensor of the present invention is manufactured as follows. A 2 cm length of 0.01 in diameter alumel wire is spot welded to a length of 0.01 in diameter chromel wire. The chromel wire is cut off at 5.5 mm from the weld junction, and the protruding wires at the weld made no longer than 0.5 mm. The chromel section is bent into a U form and another alumel section is welded to the chromel section. The alumel is again cut to a length of 5.5 mm. This procedure is continued until four junctions have been assembled and the final alumel wire cut to a length of 2 cm. This structure is then bent into a cloverleaf pattern to form the final sensor. The thermocouple junctions of the formed sensor are next oxidized in an air oven at 750° C. for 30 min to set the form of the sensor relieve stresses and provide an oxidized surface for application of the catalyst.

An γ-alumina gel prepared as described below is next applied as a bead to the first and third junction of the sensor.

The γ-alumina used in the preparation of the catalytic junction was a γ-alumina powder obtained from Kaiser Chemicals, Baton Rouge, Louisiana, and designated as A-300 Ground. This γ-alumina has a specified surface area of 260 $m^2g^{-1}$, a particle size of less than 45 μm, and low impurity levels, particularly $Na_2O$ at 0.4%. This material is available commercially. Any similar γ-alumina will probably substitute, the important specifications being the particle size and the impurity levels. The latter may poison the platinum catalyst. This γ-alumina powder is used to form a dilute aqueous alumina sol which is combined with the original γ-alumina powder to form a thick gel that can be readily applied to the sensor to form a high surface area γ-alumina bead.

To prepare the sol a 2 liter ball mill is loaded with 200 g of Kaiser A-300 γ-alumina, 400 ml of distilled water, and 25 ml concentrated nitric acid. The ball mill used was a Norton High α-Alumina grinding jar, No. 773-00. Norton cylindrical Burundum grinding balls, 13/16 in × 13/16 in, filling ⅓ of the jar, were used as grinding media. The milling was done on a Norton 753-RM constant speed drive which rotated the mill at 100 rpm. The mixture is milled for at least 30 hrs. The resulting sol is stored in a capped vessel.

The γ-alumina gel is prepared by mixing 100 g of the prepared γ-alumina sol (50.1%), 10.8 g $Al(NO_3)_3.9H_2O$ (5.4%) and 89.0 g of Kaiser A-300 ground γ-alumina (44.5%). The aluminum nitrate should be dissolved in the γ-alumina sol, and the sol added to the A-300 γ-alumina powder to obtain a thick gel-like paste that can be easily applied to the thermocouple junctions. The gel thickness is adjusted by adding more sol or γ-alumina powder.

The gel is applied to the first and third thermocouple junctions and is made to extend part of the way up the thermocouple wires. The actual bead size does not appear to greatly affect performance of the sensor. The sensor is next placed upright in a ceramic holder and dried at 100° C. for 20 min, then heated to 600° C. in air for 1 hr.

Next, a drop of platinum solution is applied to the cold γ-alumina beads and the bead soaked for 10 seconds. The platinum solution used was a solution of approximately 4.3 g of $H_2PtCl_6.3H_2O$, and sufficient water to obtain a solution weight of 5.0 g. The excess solution is completely removed from the γ-alumina bead by blotting with a soft paper towel. The impregnated bead is then treated with $H_2S$ until the bead turns from yellow to black. This may best be done by placing the sensors inside a container and passing $H_2S$ into the container.

The sensors are then dried at 100° C. for 20 min and then heated in air to 500° C. for 1 hr.

Alundum gel is next similarly applied to the second and fourth reference junctions of the sensor and the sensor is dried at 100° C. for 20 min and then heated in air to 500° C. for 1 hr.

To prepare the alundum reference junction coating the ball mill described earlier is loaded with 150 g of Fischer Alundum Cement, 30.0 g of $Al(NO_3)_3.9H_2O$, 50.0 ml of distilled water, 3.5 cc of concentrated nitric acid, and this mixture is milled for 24 hrs. The Alundum cement used in the mixture was obtained from Fischer Scientific Company. This cement is probably an α-alumina of very low surface area and no porosity. Alundum powder or α-alumina from a variety of sources can be substituted. For this application, the particle size is important, and should be in the range of 50 μm or smaller. The nitric acid used in this mixture was a reagent grade $Al(NO_3)_3.9H_2O$ from Fischer Scientific Company. This mixed thick slurry is removed from the mill and bottled. At this point, the sensor is complete, and can be attached to the ceramic base.

The sensor prepared according to this method was found to be relatively insensitive to sulfur poisoning and was able to operate at elevated temperature for extended periods of time.

Certain modifications and improvements will occur to those skilled in the art upon reading this specification. It will be understood that all such improvements and modifications have been deleted herein for the sake of conciseness and readability but are properly covered within the scope of the following claims.

We claim:

1. A method of manufacturing a combustibles sensor which is relatively insensitive to sulfur poisoning comprising the steps of:

providing a first temperature measurement device which has a temperature varying electrical property;

coating said temperature measurement device with a gel to form a high surface area substrate with increased surface area over said temperature measurement device;

coating said gel high surface area substrate with a catalytic material; and treating said catalytic material coating with $H_2S$ to achieve a high surface area of the catalytic material.

2. The method of claim 1 including the further steps of:

providing a second temperature measurement device which has a temperature varying electrical property;

connecting said first temperature measurement device to said second temperature measurement device to form a differential temperature measurement device; and coating said second temperature measurement device with a low surface area cement to form a non-catalytic surface.

3. The method of claim 1 wherein said gel is a mixture of γ-alumina and a binding agent consisting of a colloidal suspension of the γ-alumina.

4. The method of claim 1 wherein said coating of said high surface area substrate is done with a solution of chloroplatinic acid and water.

5. The method of claim 4 wherein said treating of said catalytic material with $H_2S$ is continued until the catalytic coating turns from yellow to black.

6. The method of claim 5 further including after said treating said catalytic material the steps of:

drying said treated catalytic material at approximately 100° C. for approximately 20 min; and heating said dryed catalytic material in approximately 500° C. air for approximately 1 hr to oxidize any free sulfur or metal sulfides in the device.

7. The method of claim 2 further including after said step of coating said second temperature measurement device the further steps of:

drying said differential temperature measurement device at approximately 100° C. for approximately 20 min; and heating said differential temperature measurement device in approximately 500° C. air for approximately 1 hr.

8. The method of claim 2 wherein said coating of said second temperature measurement device is done with Alundum cement having a particle size of 50 μm or smaller.

9. The method of claim 1 wherein said first temperature measurement device is a Chromel-Alumel thermocouple.

10. The method of claim 2 wherein said first and second temperature measurement devices are Chromel-Alumel thermocouples.

* * * * *